United States Patent [19]
Roteliuk et al.

[11] Patent Number: 6,045,512
[45] Date of Patent: Apr. 4, 2000

[54] SYSTEM AND METHOD FOR CONTINUOUS ESTIMATION AND DISPLAY OF CARDIAC EJECTION FRACTION AND END DIASTOLIC VOLUME

[75] Inventors: Luchy D. Roteliuk, Lake Forest, Calif.; Russell McKown, Richardson, Tex.

[73] Assignee: Baxter International Inc., Deerfield, Ill.

[21] Appl. No.: 09/094,390

[22] Filed: Jun. 9, 1998

[51] Int. Cl.[7] .............................. A61B 5/02; A61B 5/04; A61B 5/00

[52] U.S. Cl. ........................ 600/505; 600/465; 600/474; 600/526; 600/549

[58] Field of Search ...................... 600/505, 504, 600/507, 526, 474, 465, 438, 454, 508

[56] References Cited

U.S. PATENT DOCUMENTS

| | | |
|---|---|---|
| 4,236,527 | 12/1980 | Newbower et al. . |
| 4,507,974 | 4/1985 | Yelderman . |
| 4,632,125 | 12/1986 | Webler et al. ........................ 600/505 |
| 4,745,928 | 5/1988 | Webler et al. ........................ 600/505 |
| 4,858,618 | 8/1989 | Konno et al. . |
| 5,009,234 | 4/1991 | Alt ........................................ 600/485 |
| 5,146,414 | 9/1992 | McKown et al. . |
| 5,383,468 | 1/1995 | Nakayama et al. .................. 600/526 |
| 5,687,733 | 11/1997 | McKown . |

*Primary Examiner*—Cary O'Connor
*Assistant Examiner*—Navin Natnithithadha
*Attorney, Agent, or Firm*—Jeffrey Slusher; Lena I. Vinitskaya

[57] ABSTRACT

The cardiac ejection fraction EF is estimated based on the parameters of a model of an indicator (such as thermal) dilution through the heart. A channel model is defined by an upstream indicator injector, such as a heater, positioned preferably in the right atrium/ventricle and a downstream indicator concentration sensor, such as a thermistor. The preferred model is a lagged normal transfer function, which has as one of its output parameters the indicator decay constant $\tau$ of the blood channel. The heart rate HR is also measured. The ejection fraction EF is then calculated continuously as $EF = 1 - \exp(-60/(\tau^* HR))$. The cardiac output CO is also estimated in the model, preferably based on an estimate of the zero-frequency gain of the lagged normal transfer function. End diastolic volume EDV is then also calculated continuously as a function of CO, HR and EF. In applications where the step response of the indicator concentration sensor is slow relative to the indicator decay, the transfer function Hs of the sensor is determined ahead of time. Parameters characterizing Hs are then stored in a memory device and the measured transfer function data is scaled by Hs prior to modelling to provide the most accurate EF estimate.

16 Claims, 4 Drawing Sheets

SYSTEM AND METHOD FOR CONTINUOUS ESTIMATION AND DISPLAY OF CARDIAC EJECTION FRACTION AND END DIASTOLIC VOLUME

BACKGROUND OF THE INVENTION

1. Field of the Invention

This invention relates to the in-vivo determination and display of estimates of the cardiac ejection fraction, or the end diastolic volume, or both.

2. Description of the Related Art

Information about the output of a patient's heart is very valuable to a surgical team operating on the patient or to physicians who are trying to diagnose an illness or monitor the patient's condition. Few hospitals are therefore without some form of conventional equipment to monitor cardiac output.

One common way to determine cardiac output is to mount some flow-measuring devices on a catheter, and then to thread the catheter into the patient and to maneuver it so that the devices are in or near the patient's heart. Some such devices inject either a bolus or heat at an upstream position, such as in the right atrium, and determine flow based on the characteristics of the injected material or energy at a downstream position, such as in the pulmonary artery.

For example, U.S. Pat. No. 4,236,527 (Newbower et al., Dec. 2, 1980) and U.S. Pat. No. 4,507,974 (Yelderman, Apr. 2, 1985), describe systems for measuring cardiac output in which heat is used as an indicator. In such heat-based systems, a balloon catheter is typically positioned proximal to the branch of the pulmonary artery via the right atrium and the right ventricle. The catheter includes a resistive heating element, which is positioned in the atrium and/or ventricle, and a thermistor, which is positioned in the artery. Cardiac output is then calculated as a function of the sensed downstream temperature profile.

U.S. Pat. No. 5,146,414 (McKown, et al., Sep. 8, 1992) describes a system in which the transfer function of the channel (the region from where an indicator such as heat is applied to the blood upstream to the downstream position where the indicator concentration, such as temperature, is sensed) is modeled, the approximate spectrum of the noise is determined, and the output of the system is used in a feed-back loop to adaptively update the parameters of the model and thus to improve the estimate of cardiac output (CO). U.S. Pat. No. 5,687,733 (McKown, et al., Nov. 18, 1997) describes an improvement over the earlier McKown '414 system that estimates both the CO trend and an instantaneous CO value. Moreover, in the McKown systems, only the zero-frequency (dc or steady state) gain of the channel is required to get an estimate of the cardiac output (CO).

Although these known systems provide estimates of cardiac output with varying degrees of accuracy, they fail to provide any estimate of the heart's ejection fraction (EF), which is defined as the ratio between the stroke volume (SV) of the heart and its end diastolic volume (EDV). The ejection fraction is thus a measure of how efficiently the heart pumps out the blood that it can contain.

Because of its diagnostic importance, there are several known methods for measuring EF. Such systems, however, frequently rely on the use of an injected bolus and on evaluation of the wash-out (thermodilution) curve in the blood vessel. U.S. Pat. No. 4,858,618 (Konno, et al., issued Aug. 22, 1989), for example, describes a thermodilution system for determining right ventricular ejection fraction. In this known system, a cold bolus indicator is injected into the right ventricle. Pre- and post-bolus temperatures and sensed in the pulmonary artery. The temperature differentials are used to determine the ejection fraction.

One problem with using a bolus to determine EF is that it is difficult to establish just where on the sensed bolus curve the measurements are to begin, since the front side of the curve depends heavily on mixing, on the heart rate, and even on how fast the administering nurse is pushing the syringe plunger while injecting the bolus. Another problem faced by all such known systems is that they require synchronization with the heart cycle in order to reduce the effects of the heartbeat when producing an EF estimate. Some systems synchronize based on plateaus in the wash-out curve, but this presupposes a fast and very accurate thermistor. Other systems rely for synchronization on an EKG trigger. EKG synchronization, however, is difficult, since it is then necessary to slave in and precisely coordinate the timing of other instruments, each gathering its own data.

Further problems of existing systems for determining EF stem from their need to identify discrete plateaus in the dilution profiles created by the heart beats. This is necessary because these systems use the plateaus as markers in order to fit exponential or ratio-based curves to the data, which are in turn used to evaluate the dilution decay. This approach is accurate in practice, however, only for a relatively slow heart rate and a thermistor whose response is significantly faster than the decay parameter $\tau$.

In effect, these conventional systems assume a square-wave dilution curve. This is, however, usually an unrealistic assumption. First, most of the patients needing EF measurements in a hospital are not in the best of health; rather, they tend to have relatively high and erratic heart rates. Furthermore, in systems that use a bolus of relatively cold fluid, the sensed heart rate is likely to be incorrect since the cold bolus itself tends to affect not only the heart rate, but also its regularity. Second, real thermistors distort the plateaus, so that the exponential fits themselves become distorted. Third, as the EF rises, the drops in the plateaus also rise. This causes the systems to use fewer plateaus, and thus reduce their accuracy, because of the limited signal-to-noise ratios of these systems.

What is needed is therefore a system that can produce continuous estimates of the EF or EDV, or both. This invention provides such a system.

SUMMARY OF THE INVENTION

According to the invention, the cardiac ejection fraction EF is estimated based on indicator dilution by injecting an indicator such as heat into the blood at an upstream position (preferably, the right atrium/ventricle) in a heart according to a predetermined indicator driver signal x(t) and by using an indicator sensor, such as a thermistor, to sense a local indicator concentration, such as temperature, of the blood at a downstream position (preferably, the right branch of the pulmonary artery). The indicator sensor generates an indicator concentration signal y(t) corresponding, as its name implies, to the locally sensed concentration of the indicator. The region from and including the upstream position to and including the downstream position forms a channel for the blood. The heart rate HR, or, preferably, an average heart rate HR_avg, is also measured by a heart rate monitor or a sub-processor.

A model of the channel is built up and calculated by a processor as a predetermined function of the indicator signal x(t) and the indicator concentration signal y(t). The model is preferably of the lagged normal transfer function Hxy, which has output parameters including both the zero-frequency gain value dc and the indicator decay parameter $\tau$ of the modelled channel transfer function Hxy. The cardiac ejection fraction EF of the heart is then estimated continuously as a predetermined function of the heart rate and of the decay parameter $\tau$. Preferably, EF is calculated as EF=1−exp(−60/($\tau$*HR)).

The invention is also able to estimate the end diastolic volume of the heart. To do this, a cardiac output CO value is also continuously estimated by the processor preferably as a function of the zero-frequency gain of the channel transfer function. The end diastolic volume (EDV) value is estimated by the processor as a function of the CO values, the ejection fraction, and the heart rate.

One embodiment of the invention uses a fast indicator sensor (such as a thermistor), meaning that its step response is faster than the decay parameter $\tau$. In this embodiment, the indicator concentration y(t), before it is used in the channel model, is passed to the processor for inclusion in the model calculations through an open bandwidth front end filter, which acts as a low-pass filter to reject only frequency components near, at or above the Nyquist sampling frequency. This presents substantially "raw" indicator data to the processor.

In another embodiment of the invention, the indicator sensor is slower. To prevent this from affecting the accuracy of the EF and other calculations, the transfer function Hs of the sensor may be determined at the time of manufacturing the catheter (for example) on which the sensor is preferably mounted. Parameters characterizing this transfer function Hs are then prestored in a memory device. The effect of the slow sensor response on the EF calculations is then eliminated or at least greatly reduced by applying the "inverse" of the sensor transfer function Hs to the channel transfer function Hxy, in essence "defiltering" the indicator concentration signal y(t) to recreate "raw" indicator data.

DETAILED DESCRIPTION

Figure 1:
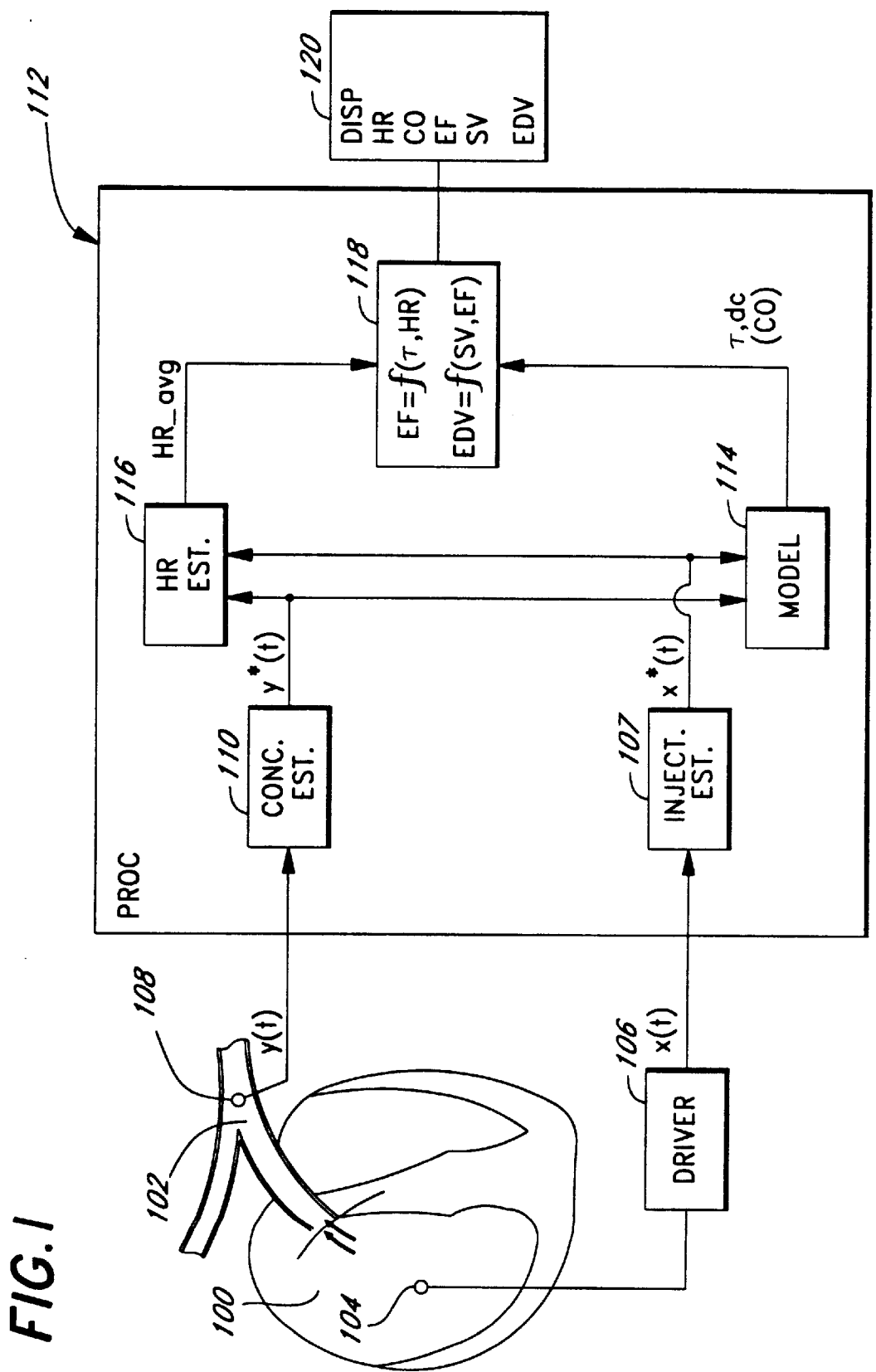
FIG. 1 is a block diagram of a first embodiment of a system according to the invention for continuous estimation of the ejection fraction, or end diastolic volume, or both, of a patient's heart, in which a fast-response indicator sensor is used for measuring the indicator response of the blood, and in which the patient's heart rate is estimated by the system itself.

In broadest terms, the components that make up the system according to the invention include an indicator driver/sensor pair that injects an indicator at an upstream position in the heart (preferably, the right atrium) and senses an indicator concentration signal at a downstream position (preferably, the right branch of the pulmonary artery). After conditioning the signal sensed by the indicator sensor, cardiac output CO is estimated to generate an indicator wash-out or decay parameter $\tau$ that is included in a set of parameters that characterize the indicator response of the channel (the blood path between the indicator driver and the sensor). Note that the indicator driver signal may be generated in many different forms: continuous, impulsive, deterministic, repetitive, pseudo-random or even random.

The patient's average heart rate HR is also sensed and preferably averaged as HR_avg over the same observation interval that is used for the as $\tau$ estimate. The decay parameter $\tau$ and HR_avg are then used to calculate a continuous estimate of the heart's ejection fraction EF, in particular, of the right heart.

In order to estimate the heart's end diastolic volume, the invention also needs an estimate of CO. In the preferred embodiments of this invention, CO is determined using the method and system described in McKown '733. One advantage of this choice is that the McKown '733 system provides a CO (as well as $\tau$) estimate continuously. Another advantage is that it is more accurate than other conventional alternatives. Still another advantage is that it is more stable than other known systems in the presence of the many noise sources found in the environment that is typical when there is a need to measure CO. These advantages stem in large part from the fact that the lagged normal model uses the entire observation (data collection) interval, so that the lagged normal model tends to be less noisy and can more accurately determine the decay parameter $\tau$.

Moreover, unlike other systems, the McKown '733 system not only bases its estimations on a complete model of the channel, but it also updates its parameters recursively. One advantage of this is that the complete channel model does not discard the wealth of information lost in other conventional systems. Furthermore, because of recursion, all of the sensed data is "used" all of the time, since even past data is incorporated into current updates.

In order to understand this invention fully, it is helpful to understand at least some of the theory underlying the CO estimation routine used in McKown '733 (see the patent itself for a complete explanation). A brief summary therefore follows:

In the context of estimating cardiac output, the "lagged normal model" described by Bassingthwaighte, et al. in "Application of Lagged Normal Density Curve as a Model for Arterial Dilution Curves," Circulation Research, vol. 18, 1966, has proven to be particularly accurate and useful, and it is therefore the model for cardiac output used in McKown '733. The lagged normal model is defined as a linear, time-invariant system (LTIS) whose impulse response is the convolution of a unity-area Gaussian (normal distribution) function and a unity-area decaying exponential. The Gaussian has two parameters: the mean $\mu$ and the standard deviation $\sigma$. The exponential has one parameter: the time-decay parameter $\tau$. The unity-gain, lagged-normal transfer function H_LN at each frequency $\omega$ sampled ($\omega$ is the independent variable in this model) thus depends on $\mu$, $\sigma$, and $\tau$ as follows:

$$H\_LN(\omega|\mu,\sigma,\tau)=\exp[-j*\omega*\mu-(\omega*\sigma)^2/2]/(1+j*\omega\tau)$$

where exp is the exponential function and the physical meaning of the parameters is:

μ: a pure time delay that represents translational flow
σ: a measure of random dispersion
τ: a time constant associated with mixing in a distribution volume, which, in this example, is the blood vessel The units of $\mu$, $\sigma$, and $\tau$ are time (seconds) and the units of $\omega$ are radians per second.

Although other indicators may be used, in the preferred embodiment of the McKown '733 system, heat is used as the indicator, and the indicator driver signal is a pseudo-random binary sequence (PRBS). The driver/sensor pair therefore preferably consists of a heater and a thermistor. H_LN is estimated as an optimized fitting of a vector of complex values $Hxy(\omega_n)$, each representing a measurement of the transfer function between a heater power signal x and a thermistor temperature signal y. Each vector element contains the parameters fitted to the measured temperature data at each of ten frequencies $\omega_n$ (the first ten PRBS harmonics). If $\mu$, $\sigma$, and $\tau$ are known, then each of the ten complex measured numbers $Hxy(\omega_n)$ would individually provide an estimate of cardiac output CO according to:

$$CO(n)=K*H\_LN(\omega_n)/Hxy(\omega_n) \text{ for } n=1 \text{ to } 10$$

where K is a known or experimentally determinable conversion constant.

In order to apply this relationship, the McKown '733 system first determines not only what the values of $\mu$, $\sigma$, and $\tau$ should be, but also how the ten cardiac output estimates CO(n) should be combined. One should note that the cardiac output does not depend on the shape of $H(\omega)$, or $Hxy(\omega)$, but only on the zero-frequency gain, dc of Hxy. Since the experimental transfer function Hxy is measured at ten frequencies $\omega_n$ that are not zero, however, the McKown '733 system in essence extrapolates the measured $Hxy(\omega)$ to zero frequency. A simplex (for example) optimization routine is then used to provide a best fit of the ten modelled transfer function values H_xy to the observed values. The relationship shown above for CO can then be reduced to CO=K/dc, where dc is the zero-frequency ($\omega$=0) gain value in units of degrees Celsius per watt, and K is the experimentally determined constant that is approximately equal to 0.0158 and has the unit (liters per minute)/(degrees Celsius per watt).

Thus, the dc value is of importance primarily to obtain a CO estimate. Since this is the measurement of greatest interest in the McKown '733 system, tests, experiments and experience have shown that the optimization routine used may in many applications be speeded up with negligible loss of accuracy by constraining one or more parameters, for example, by constraining $\sigma$ to be a linear function of $\tau$. The inventors of this invention hypothesize that it may be possible to improve both speed and accuracy either by removing the constraints, by constraining other parameters, or by changing the constraint on $\sigma$. A two-pass optimization may also prove beneficial in some applications. For example, using the existing optimization routine of the McKown '733 system, one might first impose the constraint on $\sigma$ in a first pass to quickly get an accurate dc value, and then use the dc value in a different routine, with possibly different constraints, to calculate the other parameters such as $\tau$.

Of importance to understanding this invention is, however, that the McKown '733 system provides a continuous CO value (equivalently, the dc value), as well as the decay parameter $\tau$. Note that "continuous" does not here mean that displayed values are "continuously changing," but rather that they can be updated every processing cycle (preferably a PRBS cycle), after an initialization period.

The McKown '733 system is preferred for the reasons given above, and because it in fact already exists. Any other system capable of providing the transfer function (impulse response) of the channel may, however, be used instead, provided that the system also generates values from which CO (or dc) and $\tau$ can be determined, since these values are used in this invention to calculated EF and EDV as described below.

In the following description of the various embodiments of the invention, it is assumed that heat is used as the indicator that is injected into the blood. As such, the upstream indicator driver is a heating element and the downstream indicator sensor is a thermistor. This is the preferred choice because this technology is well-established and was the choice in a prototype and tests of the invention. Using the method described in McKown '733, moreover, using heat as an indicator gives highly accurate CO estimates. Nonetheless, heat is but one possible indicator that may be used in this invention. As long as the indicator injector and sensor used generate measurable and sufficiently well-defined and non-noisy signals (which can be determined by normal experimentation), then the signals may be used in this invention with no or only easily realizable modifications to the rest of the system.

As one example of a different indicator that may be used in this invention, known luminescent materials may be injected into the patient's heart instead, using known devices. Luminescence may then be sensed downstream, also using known sensors, and the variation in luminescence may serve as an indicator concentration signal. Weakly radioactive dyes or agents may be used similarly.

As another example, in the preferred embodiment of systems such as Yelderman's or the McKown '733 system, heat is injected according to a pseudo-random binary sequence (PRBS). It is, however, also possible to inject fluids so as to follow a similar injection pattern. As long as the injection period is slow enough, small boluses may, for example, be released into the blood stream so as to approximate a PRBS profile, and the concentration of the bolus material may be sensed downstream using corresponding known sensors to establish an indicator concentration signal. In sum, as long as the indicator injector and sensor used generate measurable and sufficiently well-defined and non-noisy signals (which can be determined by normal experimentation), then the signals may be used in this invention with no or only easily realizable modifications to the rest of the system.

FIG. 1 is a block diagram of a first embodiment of a system according to the invention for continuous estimation of the ejection fraction, or end diastolic volume, or both, of a patient's heart. For accurate measurement of the cardiac output CO of a patient, especially using the McKown '733 system, it is advantageous to inject an indicator into the blood in or near the patient's right atrium/ventricle 100 and to sense an indicator concentration signal in or proximal to the branch of the pulmonary artery 102. These injection and sensing positions are therefore assumed below in order to illustrate the preferred embodiments of the invention. The flow of blood from the right atrium/ventricle and through the pulmonary artery is indicated in FIG. 1 by the parallel arrows.

In order to increase accuracy, it is preferable to use a heat signal as the basis of a measurement of the cardiac output CO. As is explained above, however, this is only one possible indicator that may be used. An indicator driver or injection device 104 is positioned in the right atrium 100. In the preferred embodiment in which the indicator is heat, the indicator driver is an electrical heating element 104. The heating element 104 is preferably an electrically resistive element whose temperature is determined by the current or voltage supplied to the element via a driving circuit 106, which drives the heating element 104 so that its temperature follows a predetermined signal profile.

In the preferred embodiments of the invention, the indicator signal (preferably, temperature) profile x(t) that the indicator driver (preferably, heater) follows is as described in the McKown '733 patent. In this system, as in the Yelderman system also mentioned above, the heat signal is generated based on a pseudo-random binary sequence (PRBS) in order or provide an efficiently detectable heat signal at the downstream sensing position, with a high spectral content yet with low and therefore trauma-reducing average applied heat. Moreover, although the heat signal is pseudo-random, it is still at all times known to the system, so that the characteristics of the calculations based on it are well understood and well conditioned.

In practical applications, the injection device 104 cannot exactly follow the desired injection profile as directed by the driver 106. For example, a heating element cannot exactly follow a square-wave pattern because of lags in heating up and cooling down the heating element. Consequently, the invention preferably includes a drive signal estimation subsystem 107 that generates an estimated indicator drive signal x*(t) that corresponds to the desired injected indicator profile x(t). In the context of thermodilution, for example, the power output by the metal in the heating element is itself temperature-dependent, due to the properties of the metal (for example, nickel) used as the resistive element. One way to estimate x*(t) is thus to measure both the voltage over and the current through the heating element. Multiplying the two will give a good estimate of the actual amount of indicator (here: heat) applied to the blood.

An indicator concentration sensor 108 is positioned at the downstream position in the pulmonary artery 102. In the preferred embodiment in which the indicator is heat, the sensor is a thermistor or some similar temperature-sensing element 108. The heating element 104 and the thermistor 108 are preferably mounted spaced apart at or near the distal end of a catheter, which is then fed into a vein of the patient and threaded into and through the vein until the heating element and the thermistor reach their operating positions. This technique is well known and is therefore not described further.

Conventional power and clock devices are preferably included to supply electrical power and timing signals to the driving circuit 106 and the other components of the invention. These devices are neither illustrated nor described further since they are well known.

The electrical output signal from the thermistor 108—the indicator concentration signal y(t)—is applied as an input signal to a concentration estimation circuit or sub-processor 110 included in or electrically connected to a main processor 112. In the illustrated first embodiment of the invention, it is assumed that the thermistor 108 has a fast response, meaning that its instantaneous temperature signal closely and predictably reflects the actual instantaneous temperature of the blood whose temperature it is measuring.

The concentration estimation circuit 110 included in this embodiment of the invention is preferably the same as is used in the McKown '733 system, but with one important modification: In the McKown '733 system, the thermistor's output signal y(t) is low-pass filtered with a cut-off frequency of about 1 Hz, before sampling at 10 Hz. This low sampling bandwidth not only helps reduce noise effects, but it is also sufficient for CO calculations, since raw temperature data is not necessary to determine the parameters of the lagged normal model. This is because only the zero-frequency (dc) gain is needed and used to compute CO.

In this invention, however, the actual shape of the thermal dilution curve, that is, its instantaneous values over an entire cycle, are used to provide continuous EF estimates. As such, raw temperature data is necessary. In order to provide this raw data, the concentration estimation circuit 110 in this embodiment of the invention preferably has a much wider bandwidth than in the McKown '733 system. This increased bandwidth may range as high as the Nyquist bandwidth of half the sampling rate. In one prototype of the invention, a 3 Hz sampling bandwidth (determined by the limits of the thermistor) was used rather than the 1 Hz bandwidth in the McKown '733 system. No other filtering is necessary. Assuming the thermistor's 108 response is fast enough not to interfere with the fastest predicted possible $\tau$ value (the minimum speed can be determined through conventional experimentation), then the lagged normal model such as is used in McKown '733 will automatically provide the correct value of $\tau$.

Regardless of the thermistor used, however, the sensor (here: thermistor) used, however, the signal available for inclusion in further processing is not exact, but is, rather, an estimate of the actual concentration of indicator at the sensor. In many cases, the signal is filtered—indeed, whenever the signal is digitized, it will be "filtered" by the very nature of analog-to-digital conversion. For example, information about frequency components above the Nyquist rate of half the sampling frequency will be lost due to aliasing. Consequently, the output signal from the indicator concentration signal estimator 110 is an estimated sensed concentration signal y*(t).

The processor 112 includes a parameter modelling subprocessor 114, which is preferably the lagged normal modelling system described in McKown '733. As is summarized above and described in McKown '733, this modelling method uses cross-correlation and optimization routines to calculate an estimate of the zero-frequency (dc) gain of the channel transfer function, as well an estimate of the decay parameter $\tau$. The inputs to the modelling system 114 used in this invention are the indicator driver signal x(t) and the thermistor signal y(t), or, more accurately, their estimates x*(t) and y*(t). Its outputs are an estimate of the zero-frequency gain of the channel transfer function, and an estimate of the decay parameter $\tau$.

The processor 112 also includes or is attached to a heart rate monitor or estimation circuit 116, which preferably calculates the average heart rate of the patient's heart over an experimentally or otherwise pre-determined interval. The heart rate monitor 116 in the first embodiment of the invention illustrated in FIG. 1 is preferably a sub-processor or subroutine incorporated into the processor 112.

In this embodiment, the heart rate monitor 116 has as input signals both the estimated indicator driver signal x*(t) and the estimated indicator concentration signal y*(t). Standard signal processing techniques may then be used to obtain an average heart rate value HR_avg from the temperature signal. For example, a reliable HR measurement is obtained by computing the power spectral density (PSD) of the zero-mean temperature signal in any conventional manner. Note that the McKown '733 system includes a drift-removal routine that includes these calculations and can thus be used by the system according to this invention to provide HR. The location of the peak of the PSD in the range of the normal heart rate (known from experience) then defines the value HR, since HR=PSD_peak (Hz)*60 (beats per minute). For consistency, this should be done over the same time observation window that the parameter modelling sub-processor 114 uses. Once a number of current heart rate values are obtained, they can be averaged to produce HR_avg. The averaging is preferably carried out over the same observation interval that is used to determine $\tau$ in order minimize errors in calculating EF and EDV.

Note also that it is in some cases possible to estimate the heart rate using only the estimated driver signal x*(t). As is mentioned above, the resistance of the heating element typically is temperature-dependent. Consequently, even if a constant voltage were to be applied over the internal resistive element (made, for example, of nickel), the core temperature of the element would vary due to the cooling, pulsating (and thus non-uniform) effect of the blood surrounding the element. An HR signal is thus superimposed on the signal x*(t) alone and conventional filtering techniques may be used to identify it.

Other devices may be used to provide a value for the average heart rate HR_avg. These include conventional dedicated heart monitors, or the heart rate output of existing multi-parameter patient monitors. Although the invention does not necessarily require averaging of the heart beat, this is preferred because the smoothing effect of averaging also helps filter out irregularities without sacrificing the ability of the system to provide continuous EF estimates. As long as the average is taken over a sufficient number of heart beats, averaging also eliminates the need for synchronization with the heart cycle. In existing EF-estimating systems, four to seven heart beats are typically included in a heart rate average. In this invention, however, if the PRBS heat signal is used, several more beats may be included, since several more will normally occur during a single PRBS cycle. This further decreases the noise sensitivity of the invention as compared with known systems.

Figure 2:
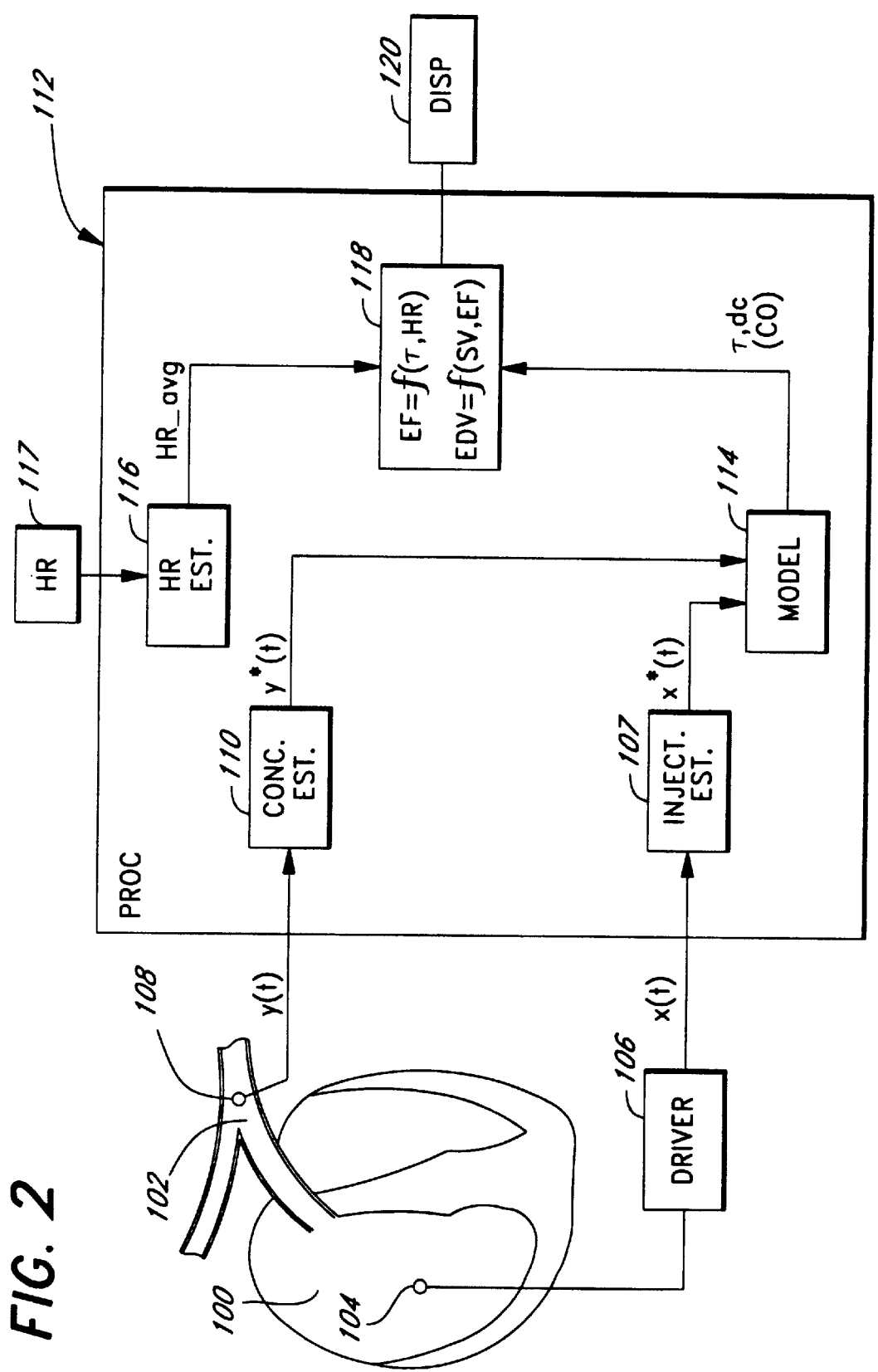
FIG. 2 is a block diagram of a second embodiment of the invention, in which a fast-response indicator sensor is used, but in which the patient's heart rate is sensed by an external device.

FIG. 2 illustrates this embodiment, the external heart rate monitor being labeled 117. Depending on the external device, the heart rate signal generated may be used directly in this invention, or it may require filtering or other conditioning either to establish the heart rate, to condition the signal for use by the other components of this invention, or both.

As FIG. 2 shows, in this case, the heart rate monitoring circuit 116 will then be modified in any conventional manner to properly condition the heart rate signal provided by the external monitor 115. Moreover, since the heart rate signal is being supplied by an external device, the estimation circuit 116 does not need x*(t) and y*(t) as inputs in order to get an accurate estimate of HR_avg.

The calculated values of dc, $\tau$, and HR_avg are applied as input signals to an EF sub-processing system 118, which is preferably incorporated in the processor 112 and implemented in software. This EF sub-system 118 then calculates an estimated EF value, and an estimated EDV value, or both, in a manner described further below. Note that it will also have available to it, or will calculate as described below, values for HR, CO, and stroke volume (SV) as well.

Once the EF and/or EDV values are calculated, they are displayed to the user on any conventional display 120, which will include any necessary conventional display driver. As desired, the display may also display the CO, HR and SV values that are available as outputs from the EF sub-processor 118. Of course, the EF/EDV values may instead, or in addition, be stored electronically in a memory, or be transmitted over a network or to other processing equipment. In the following description, several calculations will be described. it is to be understood that all of the calculated values may be multiplied by appropriate scaling constants, for example, to ensure that they will fall within some desired range for display, or to convert to different units.

Now consider an impulsive injection of heat into the right atrium/ventricle. Let $\Delta T(i)$ be the change in temperature (or in the concentration of any other indicator used) of the blood in the pulmonary artery (PA) from a baseline temperature when the heat is first injected into the heart to the temperature i heart cycles later (measured, for example, over the time from one R-wave to the next). Let $\Delta T(i-n)$ be the temperature change n R-waves earlier. It is then well known that the following relationship approximates the indicator decay curve (also known as the physiological wash-out curve):

$\Delta T(i)=\Delta T(i-n)*\exp(-t/\tau)$, where $\tau$ is the decay constant.

The physiological wash-out decay can also be represented by $(1-EF)^n$, where n is the number of heart events (for example, R-R intervals) in the observation period (often taken to be from about 80% down to about 30% of the peak value). For example, assume that the ejection fraction (EF) is 0.6 (60%). At the end of one interval there will be (1−0.6)=0.4 (40%) as much indicator (for example, heated blood) remaining in the heart. After one more interval, only 40% of this 40% will remain, that is, (1−0.6)*(1−0.6)=0.16 or 16% of the original total. Thus, the following relationship also holds:

$$\Delta T(i)=\Delta T(i-n)*(1-EF)^n$$

Time t can then be represented in terms of the heart rate HR (beats per minute) and n, so that: t=n*60/HR.

Combining these three expressions and solving for EF, one finds that:

$$EF=1-\exp(-60/(\tau*HR))$$

It is not necessary according to the invention for HR to be measured from one cardiac R-wave to the next. Rather, the average HR is preferably used, for the reasons given above. The EF value obtained by using an averaged value will then be smoother and less sensitive to heart rate irregularities, and can be updated continuously rather than only after some subsequent R-wave or other triggering cardiac event.

Observe then that the invention can estimate EF as long as it also has estimates of $\tau$ and HR (that is, HR_avg). These are, of course, the very parameters provided by the parameter modelling sub-processor 114 and the heart rate monitor 116, respectively. The EF sub-system 118 therefore determines EF by calculating the expression EF=1−exp(−60/($\tau$*HR)).

Observe further that CO=HR*SV, where SV is the stroke volume and CO is measured in units of volume (liters) per minute. This simply expresses that the amount of blood the heart pumps out in a minute is equal to the amount it pumps out on every beat (stroke) times the number of strokes per minute. Finally, note that the end diastolic volume (EDV) and the ejection fraction (EF) are related as follows:

EF=SV/EDV, which also expresses the intuitive relationship that the pumping efficiency (EF) of the heart is the ratio between how much blood the heart pumps out on every beat (contraction) and how much blood is in the heart chamber just before the beat. Rearranging this expression, one sees that EDV=SV/EF.

The EF sub-processing system 118 thus either calculates CO based on the value dc received from the parameter modelling sub-processor 114 and the predetermined conversion K, (CO=K/dc), or it accepts the value CO if this is already calculated in the parameter modelling sub-processor 114. Dividing CO by the heart rate HR (obtained from the heart rate monitor 112, the EF sub-processing system 118 then calculates SV=CO/HR, and once SV is known, the EF sub-processing system 118 may calculate EDV as SV/EF, having already estimated EF by calculating 1−exp(−60/($\Sigma$*HR)).

The EF subprocessing system 118 and the parameter modeling sub-processor 114 need not be separate units. Rather, they may both be implemented as a single processing device. Indeed, they may also be implemented simply as different software modules of the processor 112. As such, the CO and EDV calculations may be carried out in either sub-processor 114 or 118 with no effect on the results or the ultimately displayed values.

Figure 3:
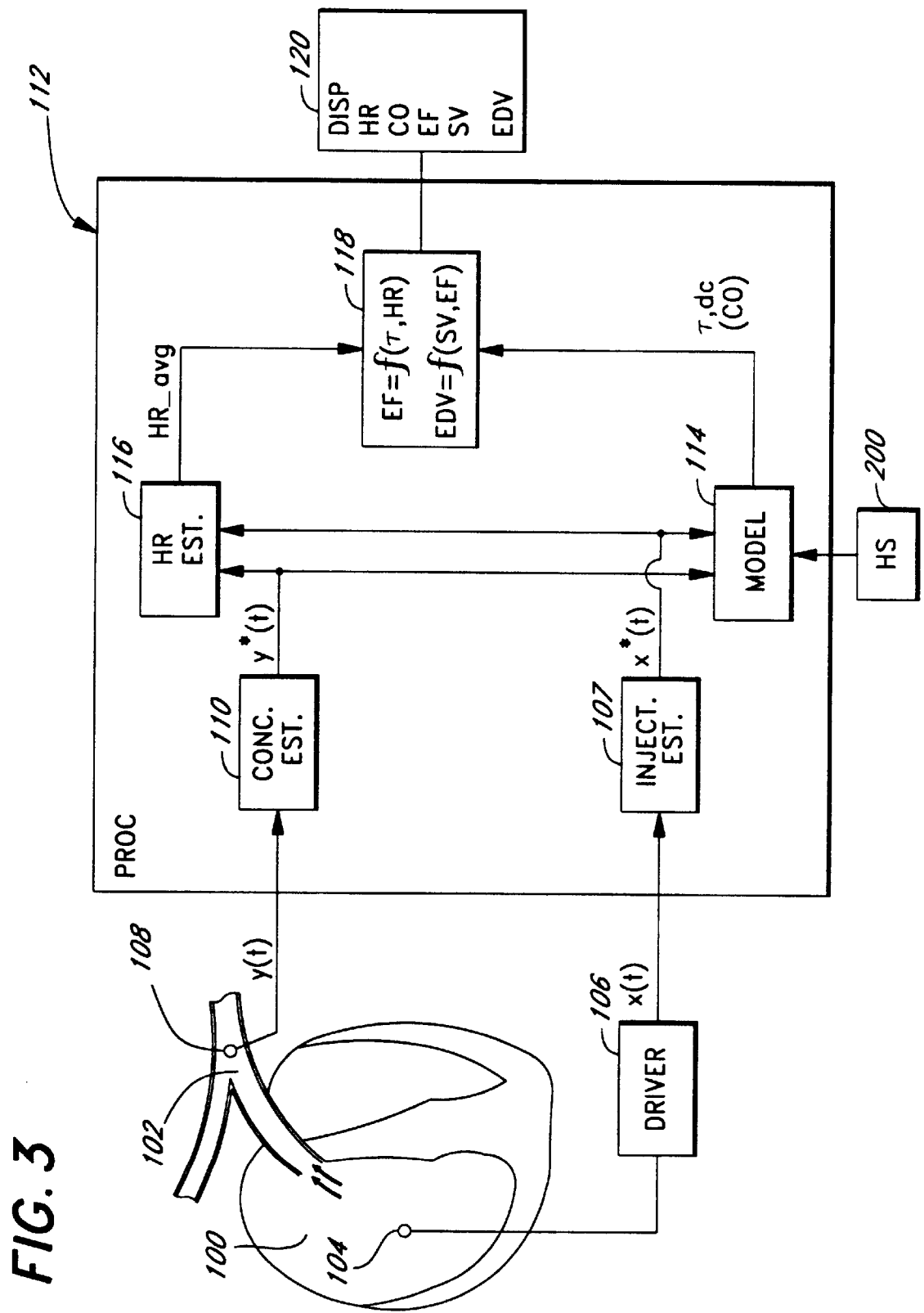
FIG. 3 is a block diagram of a third embodiment of the invention, in which a slower-response indicator sensor is used, but in which the step response of the sensor has been characterized and made available to the rest of the system. In this embodiment, moreover, the patient's heart rate is estimated by the system itself.

FIG. 3 is a block diagram showing a second embodiment of the invention. In FIG. 3, components that are essentially the same as those shown in FIGS. 1 and 2 and described above have the same reference numbers. This embodiment is preferred when the indicator sensor such as the thermistor 108 is slow compared to the thermal decay parameter. Because of this, the measurement of the exponential decay parameter $\tau$ will be affected by the slow response time of the thermistor, especially at high heart rates.

To compensate for this, according to the invention, the transfer function (equivalently: step response) of each sensor (here, thermistor) used as the sensor 108 is pre-determined, and the "inverse" of this transfer function is applied to Hxy so as to "de-filter" or compensate for the effects of the slow response time of the sensor. There are several known ways to characterize the step response of a transfer function, the easiest of which is simply to apply a series of impulse input signals to it, to measure each response, and then to average the results.

One practical way to pre-determine the transfer function (Hs) of several thermistors is to establish a multiple catheter measurement station at which several catheters (each equipped with its thermistor) are dipped from the air (for example) into a temperature-controlled bath. Using any of the many known curve-fitting techniques, one then calculates the parameters of a mathematical model of each Hs that best fit the recorded thermistor data. These parameters can then be stored, for example in a permanent memory device such as an EEPROM for each thermistor. Using this procedure, rejects could be eliminated or at least greatly reduced. In this embodiment of the invention, the values characterizing Hs are stored in such a device, which, in FIG. 3, is shown as the component 200.

The pre-computed values included in the transfer function storage device 200 are made available as an input signal to the modelling sub-processor 114 or, alternatively, to the indicator concentration estimation circuit 110. In this embodiment, the indicator concentration estimation circuit also receives as input signals the thermistor signal y(t) and the heater signal x(t) (preferably, its estimate x*(t)), which are also applied to the heart rate averaging circuit 116.

The estimation circuit 110 for the fast thermistor in the first and second embodiments of the invention (FIGS. 1 and 2) in essence operates as an open-bandwidth front-end low-pass filter with filter-to pass on "raw" thermistor data, with filtering only of the frequencies near, at or above the Nyquist frequency. In the third embodiment (FIG. 3), however, the slower thermistor itself imposes a frequency-dependent attenuation profile on its data, effectively acting as a low-pass filter itself. The system must therefore "un-filter" the data to get at the "raw" data used in the EF calculations. Recall that the McKown '733 system estimates H_LN as an optimized fitting of a vector of complex values Hxy($\omega_n$) to the observed values. This vector Hxy will still be available in this invention if the McKown '733 modeling sub-processor is used as the sub-processor 114; otherwise, Hxy (the measured transfer function of the channel), respectively should be calculated as in McKown '733 in the modelling sub-processor 114.

Now let Hxy_p be the desired, complex transfer function of the physiological wash-out of the channel (heart/blood vessel), that is, the transfer function one would have observed in the absence of the warping effect of the slow thermistor. Assume also that Hs—the pre-determined transfer function of the thermistor—is calculated at the same frequencies as Hxy. For example, in McKown '733, Hxy had ten elements, corresponding to the measured power to temperature transfer function of the channel at the first ten PRBS harmonics. This means that: Hxy=Hs*Hxy_p, so that the "raw" transfer function Hxy_p is calculated by the modelling sub-processor 114 as a ten-component scalar vector (component-by-component) division of Hxy by Hs.

Thus: Hxy_p=Hxy/Hs.

This Hxy_p data, that is, the Hxy data "scaled" by Hs, is then passed on to (if scaling is done in the estimation circuit 110) or is used by the modeling sub-processor 114 as before. This corresponds to modeling the Hxy_p data using the mathematical lagged-normal transfer function H_LN. This provides not only the same dc value, which is inversely proportional to CO, but it also provides the correct $\tau$, since the higher frequency components of the transfer function Hxy_p will have been adjusted to compensate for the slow response of the thermistor. The EF sub-processor 114 can therefore calculate EF and EDV as in the first embodiment of the invention. Also, as in the first embodiment, the computed EF/EDV values will also be continuous in the same sense as in McKown '733, that is, they will have the same initial acquisition time and update interval.

One additional problem of having a slow thermistor is that the thermistor data alone is less useful for determining the heart rate HR when HR is high. For this reason, in the third embodiment of the invention (FIG. 3), both the heater signal x(t) and the "raw," that is, "scaled" or "de-filtered," thermistor signal y(t) (preferably, their estimates x*(t) and y*(t)) are preferably supplied to the heart rate averaging circuit 116. With both signals available, correlation and other known techniques can then be applied to get a more accurate estimate of even high heart rates.

Figure 4:
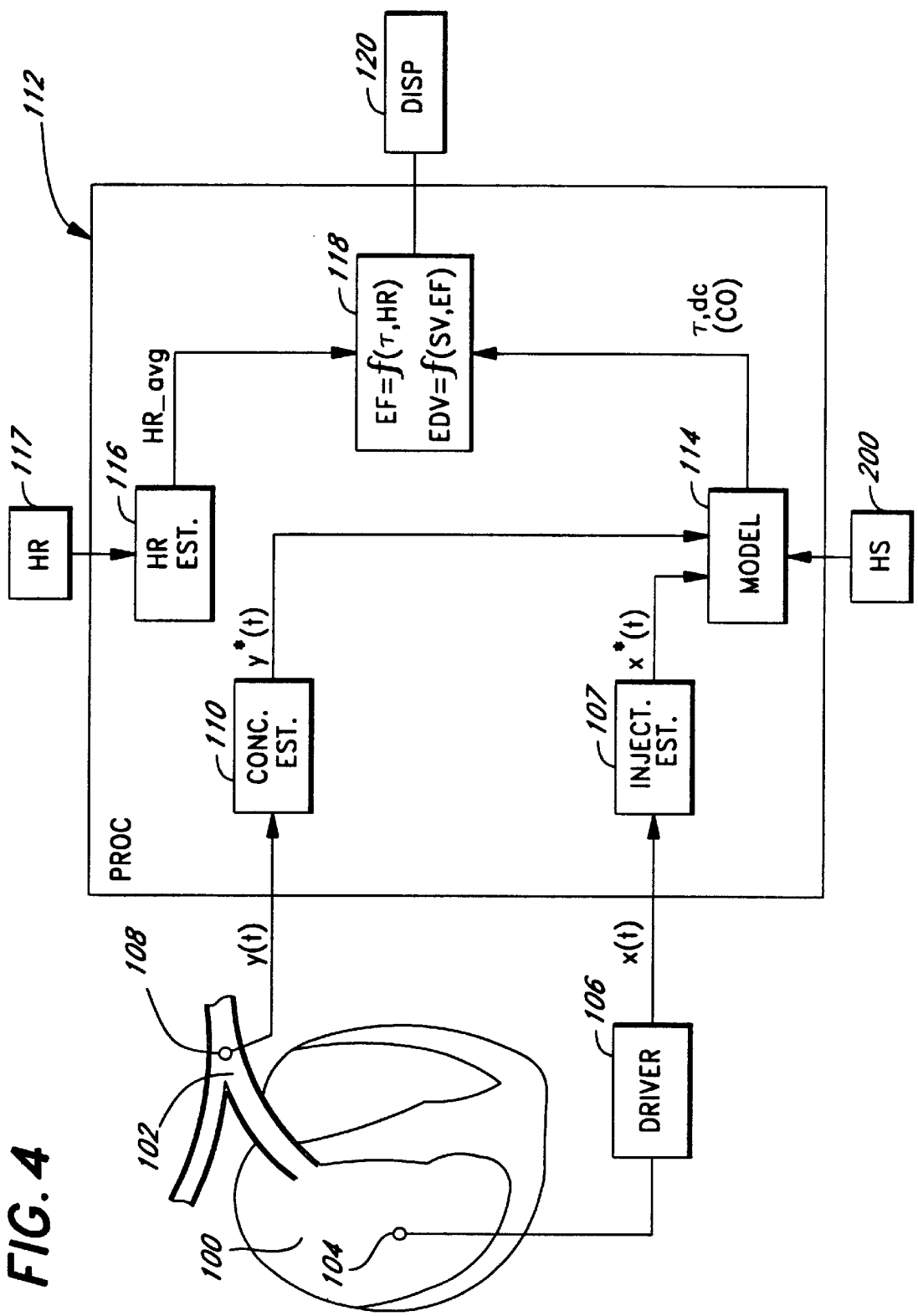
FIG. 4 is a block diagram of a fourth embodiment of the invention, in which a slower-response indicator sensor is used, but in which its step response is available, and in which the patient's heart rate is sensed by the external device.

Of course, as before, conventional external heart rate instruments may be used instead of the heat rate circuit 116 in order to provide an average HR value (HR_avg) that is independent of the characteristics of the thermistor. FIG. 4 shows, accordingly, an embodiment of the invention in which the external heart monitor 117 supplies the heart rate signal, and in which the "inverse transfer function" Hs parameters for the sensor are pre-stored.

The main difference between the first and third embodiments of the invention (FIGS. 1 and 3) and the second and fourth embodiments (FIGS. 2 and 4) lies in whether the thermistor is "fast" or "slow." In practical applications, the border between these two may be unclear. Of course, the "slow-sensor" embodiments of the invention may always be used, since they also encompass the "fast-sensor" embodiments (the transfer function Hs will simply be substantially "flat" over the entire sampled bandwidth). The slow-sensor embodiments require, however, the extra manufacturing step and cost of individual sensor calibration and the addition and programming of the memory device 200 for storing the sensor response parameters (or, equivalently, their inverses).

The decision about which embodiment to use may be made using conventional simulation and experimental techniques. For example, the heater and thermistor signals x(t) and y(t) may be generated through simulation, possibly incorporating actual data taken from patients. The parameter modeling sub-processor may then estimate τ. Alternatively, τ values may be estimated from actual measurements taken using a thermistor known to be very fast. The transfer functions Hs of representative thermistors of the type to be used in the invention can then be determined as described above. The EF values calculated with and without compensation for the Hs profiles can then be compared. If the uncompensated EF values differ by less than some predetermined amount from the compensated EF values, then the thermistors can be assumed to be fast enough and the first or third embodiment of the invention may be used.

We claim:

1. A method for estimating a cardiac ejection fraction comprising the following steps:

generating an injected indicator signal x(t) having a predetermined, time-varying signal profile and a predetermined duration;

injecting an indicator at an upstream position in a heart according to the predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR over the duration of the indicator signal x(t);

generating a model of the channel as a predetermined function of the injected indicator signal x(t) and the indicator concentration signal y(t);

continuously updating the model to provide as an output a modeled indicator decay parameter τ of the channel; and continuously estimating the cardiac ejection fraction EF of the heart as a predetermined function of the heart rate and of the modeled decay parameter τ.

2. A method as in claim 1, further including the following steps:

continuously calculating a cardiac output value CO as an output of the model; and continuously calculating an end diastolic volume value of the heart as a predetermined function of the cardiac output value CO, the heart rate HR, and the estimated ejection fraction EF.

3. A method as defined in claim 2, in which the predetermined function of the cardiac output value CO, the heart rate HR, and the estimated ejection fraction EF is proportional to the ratio of an estimated stroke volume of the heart to the ejection fraction, where the estimated stroke volume is the ratio between the cardiac output value and the heart rate.

4. A method as in claim 1, in which:

the step of injecting an indicator comprises applying heat to the blood using a heating element; and the step of sensing with an indicator concentration sensor comprises sensing local temperature of the blood at the downstream position using a thermistor.

5. A method for estimating a cardiac ejection fraction comprising the following steps:

with a heating element, injecting heat as an indicator at an upstream position in a heart according to a predetermined injected heat signal x(t);

with a thermistor, sensing a local temperature signal y(t) at a downstream position, the region from and including the upstream position to and including the downstream position forming a channel for the blood;

measuring a heart rate HR;

generating a model of the channel as a predetermined function of the injected heat signal x(t) and the sensed local temperature signal y(t);

continuously updating the model to provide as an output an indicator decay parameter τ of the channel;

continuously calculating a cardiac output value CO as an output of the model;

generating the model of the channel as a predetermined function of a measured injected heat-to-measured temperature channel transfer function Hxy by recursively determining the parameters of a lagged normal model, the parameters including both a zero-gain value dc and an indicator decay parameter τ;

pre-calculating an estimated transfer function Hs for the indicator concentration sensor;

scaling the channel transfer function Hxy by the transfer function Hs, thereby eliminating distortions due to the indicator concentration sensor;

continuously estimating the cardiac ejection fraction EF of the heart as a predetermined function of the heart rate and of the decay parameter τ.

6. A system for estimating a cardiac ejection fraction comprising the following steps:

indicator injection means for generating an injected indicator signal x(t) having a predetermined, time-varying signal profile and a predetermined duration, and for injecting an indicator at an upstream position in a heart according to a predetermined driver signal corresponding to the indicator signal x(t);

an indicator concentration sensor sensing a local indicator concentration in the blood at a downstream position and generating an indicator concentration signal, the region from and including the upstream position to and including the downstream position forming a channel for the blood;

a heart rate monitor measuring a heart rate HR over the duration of the indicator signal x(t);

processing means:

for generating a model of the channel as a predetermined function of the driver signal and the indicator concentration signal;

for continuously updating the model to provide as an output an indicator decay parameter τ of a modelled indicator dilution curve of the channel; and for estimating the cardiac ejection fraction EF of the heart as a predetermined function of the heart rate and of the thermal decay parameter τ.

7. A system as in claim 6, the processing means being further provided for:

continuously calculating a cardiac output value CO as an output of the model; and continuously calculating an end diastolic volume value of the heart as a predetermined function of the cardiac output value CO, the heart rate HR, and the estimated ejection fraction EF.

8. A system as in claim 6, in which:

the indicator injection means is a resistive heating element; and the indicator concentration sensor is a thermistor.

9. A method for estimating a cardiac ejection fraction comprising the following steps:

injecting an indicator at an upstream position in a heart according to a predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR;

generating a model of the channel as a predetermined function of the injected indicator signal x(t) and the indicator concentration signal y(t);

continuously updating the model to provide as an output an indicator decay parameter $\tau$ of the channel;

continuously estimating the cardiac ejection fraction EF of the heart as a predetermined function of the heart rate and of the decay parameter $\tau$;

generating the model of the channel as a predetermined function of a measured injected indicator-to-measured indicator concentration channel transfer function Hxy;

pre-calculating an estimated transfer function Hs for the indicator concentration sensor; and scaling the channel transfer function Hxy by the transfer function Hs, thereby eliminating distortions due to the indicator concentration sensor.

10. A method for estimating a cardiac ejection fraction comprising the following steps:

injecting an indicator at an upstream position in a heart according to a predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR;

generating a model of the channel as a predetermined function of the injected indicator signal x(t) and the indicator concentration signal y(t);

continuously updating the model to provide as an output an indicator decay parameter $\tau$ of the channel; and continuously estimating the cardiac ejection fraction EF of the heart as a predetermined function of the heart rate and of the decay parameter $\tau$;

in which the step of generating the model comprises recursively determining the parameters of a lagged normal model, the parameters including both the zero-frequency gain value dc and the indicator decay parameter $\tau$.

11. A method for estimating a cardiac ejection fraction comprising the following steps:

injecting an indicator at an upstream position in a heart according to a predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR;

generating a model of the channel as a predetermined function of the injected indicator signal x(t) and the indicator concentration signal y(t);

continuously updating the model to provide as an output an indicator decay parameter $\tau$ of the channel; and continuously estimating the cardiac ejection fraction EF of the heart as a predetermined function of the heart rate and of the decay parameter $\tau$;

in which the step of measuring the heart rate HR comprises calculating an average heart rate HR_avg.

12. A method for estimating a cardiac ejection fraction comprising the following steps:

injecting an indicator at an upstream position in a heart according to a predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR;

generating a model of the channel as a predetermined function of the injected indicator signal x(t) and the indicator concentration signal y(t);

continuously updating the model to provide as an output an indicator decay parameter $\tau$ of the channel; and continuously estimating the cardiac ejection fraction EF of the heart by calculating EF according to the following function:

EF=1−exp(−60/(AHR)), where exp is the exponential function and the heart rate is measured in beats per minute.

13. A system for estimating a cardiac ejection fraction comprising the following steps:

indicator injection means for injecting an indicator at an upstream position in a heart according to a predetermined driver signal;

an indicator concentration sensor sensing a local indicator concentration in the blood at a downstream position and generating an indicator concentration signal, the region from and including the upstream position to and including the downstream position forming a channel for the blood;

a heart rate monitor measuring a heart rate HR;

processing means:

for generating a model of the channel as a predetermined function of an injected indicator-to-sensed indicator concentration channel transfer function Hxy;

for scaling the channel transfer function Hxy by a sensor transfer function Hs, thereby eliminating distortions due to the indicator concentration sensor;

for continuously updating the model to provide as an output an indicator decay parameter $\tau$ of a modeled indicator dilution curve of the channel; and for estimating the cardiac ejection fraction EF of the heart as a predetermined function of the heart rate and of the thermal decay parameter $\tau$.

14. A system as in claim 13, further comprising storage means for storage pre-calculated parameters characterizing the indicator concentration sensor transfer function Hs, and for outputting the transfer function Hs to the processing means.

15. A system for estimating a cardiac ejection fraction comprising the following steps:

indicator injection means for injecting an indicator at an upstream position in a heart according to a predetermined driver signal;

an indicator concentration sensor sensing a local indicator concentration in the blood at a downstream position and generating an indicator concentration signal, the region from and including the upstream position to and including the downstream position forming a channel for the blood;

a heart rate monitor measuring a heart rate HR;

processing means:

for generating a model of the channel as a predetermined function of the driver signal and the indicator concentration signal;

for continuously updating the model to provide as an output an indicator decay parameter $\tau$ of a modelled indicator dilution curve of the channel; and for estimating the cardiac ejection fraction EF of the heart as a predetermined function of the heart rate and of the thermal decay parameter $\tau$;

in which the processing means includes a recursive estimator that has as output signals the parameters of a lagged normal model, the parameters including a channel indicator decay parameter $\tau$; the processing means being further provided for estimating the cardiac ejection fraction EF according to the expression EF=1−exp(−60/($\tau$*HR)), where exp is the exponential function and the heart rate HR.

16. A method for estimating a cardiac ejection fraction comprising the following steps:

generating an injected indicator signal x(t) having a predetermined, time-varying signal profile and a predetermined duration;

injecting an indicator at an upstream position in a heart according to the predetermined injected indicator signal x(t);

sensing with an indicator concentration sensor a local indicator concentration signal y(t) at a downstream position, the region from and including the upstream position to and including the downstream position forming a channel for the blood;

measuring a heart rate HR over the duration of the indicator signal x(t);

generating a model of the channel as a predetermined function of the injected indicator signal x(t) and the indicator concentration signal y(t);

continuously updating the model to provide as an output an indicator decay parameter $\tau$ of the channel; and continuously estimating the cardiac ejection fraction EF of the heart as a predetermined function of the heart rate and of the decay parameter $\tau$;

in which the step of generating the model comprises determining the parameters of a lagged normal model, the parameters including both the zero-frequency gain value dc and the indicator decay parameter $\tau$.

* * * * *